(12) United States Patent
Howell et al.

(10) Patent No.: US 7,396,948 B2
(45) Date of Patent: Jul. 8, 2008

(54) PROCESS FOR FLUORO DERIVATIVE-SUBSTITUTED ARYL PNICTOGENS AND THEIR OXIDES

(75) Inventors: Jon L. Howell, Bear, DE (US); Kevin Anthony Hay, British Columbia, CA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/644,495

(22) Filed: Dec. 22, 2006

(65) Prior Publication Data

US 2007/0106084 A1 May 10, 2007

Related U.S. Application Data

(62) Division of application No. 11/167,805, filed on Jun. 27, 2005.

(51) Int. Cl.
*C07F 9/92* (2006.01)
*C07C 41/18* (2006.01)

(52) U.S. Cl. .......................... 556/64; 556/71; 568/660; 568/661

(58) Field of Classification Search ........................ None
See application file for complete search history.

(56) References Cited

U.S. PATENT DOCUMENTS

| | | | |
|---|---|---|---|
| 3,145,222 A | 8/1964 | Brace | |
| 3,250,808 A | 5/1966 | Moore et al. | |
| 3,293,306 A | 12/1966 | LeBleu et al. | |
| 3,699,156 A | 10/1972 | Holland et al. | |
| 4,431,555 A | 2/1984 | Christian et al. | |
| 4,431,556 A | 2/1984 | Christian et al. | |
| 4,438,007 A | 3/1984 | Snyder et al. | |
| 4,454,349 A | 6/1984 | Tamborski et al. | |
| 4,681,693 A | 7/1987 | Gavezotti et al. | |
| 4,855,025 A * | 8/1989 | Gautier et al. ......... | 204/157.86 |
| 4,904,616 A * | 2/1990 | Bohling et al. .............. | 117/104 |
| 4,965,379 A | 10/1990 | Ikeda et al. | |
| 5,055,601 A | 10/1991 | Ikeda et al. | |
| 5,097,090 A | 3/1992 | Beck | |
| 5,376,289 A | 12/1994 | Montagna et al. | |
| 5,493,049 A | 2/1996 | Caporiccio | |
| 6,479,712 B1 | 11/2002 | Kawa | |
| 6,573,410 B2 | 6/2003 | Wlassics et al. | |
| 6,653,511 B2 | 11/2003 | Howell et al. | |
| 2003/0027732 A1 | 2/2003 | Howell et al. | |
| 2004/0176555 A1 | 9/2004 | Guarda et al. | |

FOREIGN PATENT DOCUMENTS

| | | |
|---|---|---|
| EP | 0 100 488 A1 | 2/1984 |
| EP | 0 100 488 B1 | 3/1987 |

OTHER PUBLICATIONS

Jeanneaux et al.; Thermal Addition of IODO-1-Perfluoroalkanes to the Perfluoroalkyl Ethylenes; Journal of Fluorine Chemistry, 4 261-70 (1974); Elsevier Sequoia S. A., Lausanne, Switzerland.

Brace; Some Approaches to the Synthesis of Fluorinated Alcohols and Esters. ii. Use of F-Alkyl Iodides for the Synthesis of F-Alkyl Alkanols; Journal of Fluorine Chemistry, 20 (1982) 313-327); Elsevier Sequoia S. A., The Netherlands.

Hajek et al.; Copper-Catalyzed Addition of Perfluoroalkyl Iodides to Unsaturated Alcohols and Transformation of the Addition Products; Journal of Fluorine Chemistry, 68 (1994) 49-56; Elsevier Sequoia S. A.

Brace et al.; Effect of a Perfluoroalkyl Group on the Elimination and Substitution Reactions of Two Homologous Series of Perfluoroalkyl-Substituted Iodoalkanes; J. Org. Chem. 1984, 49, 2361-2368; American Chemical Society.

Bravo et al.; New Methods of Free-Radical Perfluoroalkylation of Aromatics and Alkenes. Absolute Rate Constants and Partial Rate Factors for the Homolytic Aromatic Substitution by n-Perfluorobutyl Radical; J. Org. Chem. 1997, 62, 7128-7136; American Chemical Society.

* cited by examiner

*Primary Examiner*—Rosalynd Keys

(57) ABSTRACT

A process to prepare substituted aryl pnictogen derivatives comprising contacting a fluoropolyether or fluoroalkyl primary bromide or iodide, with a pnictogen derivative such as triaryl phosphine, triaryl arsine, or triaryl stibine or triaryl phosphine oxide, triaryl arsine oxide or triaryl stibine oxide, to produce the corresponding fluoropolyether- or fluoroalkyl-substituted aryl phosphine oxide, aryl arsine oxide or aryl stibine oxide; and optionally, contacting the oxide product with a reducing agent to form the corresponding substituted aryl phosphine, arsine or stibine.

21 Claims, No Drawings

PROCESS FOR FLUORO DERIVATIVE-SUBSTITUTED ARYL PNICTOGENS AND THEIR OXIDES

This is a divisional application of Ser. No. 11/167,805, filed Jun. 27, 2005.

BACKGROUND OF THE INVENTION

Due to their thermal stability, perfluoropolyether fluids have a great potential for use as engine oils, hydraulic fluids and greases. However, a drawback in their use results from the fact that certain metals are corroded by such fluids at temperatures of about 550° F. and above in an oxidative environment.

In U.S. Pat. No. 4,454,349, the preparation of perfluoroalkylether-substituted phenyl phosphines, having the structure of Formula 1 below, is described:

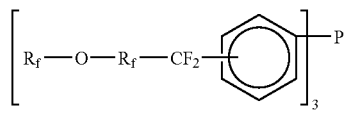

Formula 1 wherein
$R_f$—O—$R_f$ is a perfluoroalkyl ether group containing at least one ether linkage. Examples of $R_f$—O—$R_f$ included:
$C_3F_7O[CF(CF_3)CF_2O]_xCF(CF_3)$—,
$C_2F_5O(CF_2CF_2O)_yCF_2$—, and
$CF_3O(CF_2O)_zCF_2$—, wherein
x, y, and z are zero or an integer having a value of 1 to 20 and preferably 1 to 4.

Such phosphine derivatives are disclosed as being corrosion and oxidation inhibitors in polyfluoroalkylether polymeric fluids in long-term and wide temperature range applications. Temperature ranges are typically −100° F. to greater than 550° F., (−73° C. to greater than 288° C.). Incorporation of these compounds in perfluoroalkylether fluids inhibits the oxidation-corrosion of various metals with which the fluids come into contact. These additives also prevent decomposition of such fluids when exposed to a high-temperature oxidative environment.

The effectiveness of perfluoropolyether-substituted phosphines as oxidation inhibitors in perfluoropolyether fluids is well known to those skilled in the art and has been described and quantified in several patents, for instance by Snyder, et al., in U.S. Pat. Nos. 4,438,006 and 4,438,007, and by Christian, et al., in U.S. Pat. Nos. 4,431,555, and 4,431,556. Perfluoroalkyl substituted phosphines have been used in fluorous phase catalyst systems, Hope, et al., *Polyhedron* 18(22), 1999, pp. 2913-2917.

However, the synthesis described in U.S. Pat. No. 4,454,349 involves multiple steps requiring the use of hazardous and pyrophoric reactants and reaction temperatures ranging between −80° C. and 200° C. The process includes two reaction steps requiring n-butyllithium and an intermediate sulfur tetrafluoride/hydrogen fluoride fluorination step. Consequently, such potentially useful perfluoroalkyl substituted phenyl phosphines have remained effectively inaccessible.

The mechanism of free-radical perfluoroalkylation of aromatics has been studied and discussed by Bravo et al., in *Journal of Organic Chemistry*, 62(21), 1997 pp. 7128-7136. Bravo et al. studied the reaction of a perfluoroalkyl iodide (such as perfluoro-n-butyl iodide) with various aromatic compounds, including benzene and biphenyl.

It would be desirable to improve the synthesis of the perfluoroalkyl and perfluoropolyether-substituted aryl phosphines, such as the phenyl phosphines described above, and to have available the antimony and arsenic analogs. The present invention provides such a process.

SUMMARY OF THE INVENTION

The present invention provides a process to prepare a substituted aryl pnictogen, and its corresponding oxide. The process comprises (a) contacting a compound selected from the group consisting of fluoropolyether primary bromide, fluoropolyether primary iodide, fluoroalkyl primary bromide and fluoroalkyl primary iodide, with a triaryl phosphine, triaryl arsine, triaryl stibine, triaryl phosphine oxide, triaryl arsine oxide, or triaryl stibine oxide to produce the corresponding mono-substituted, di-substituted, tri-substituted, or a combination of two or more thereof, fluoropolyether- or fluoroalkyl-substituted aryl phosphine oxide, aryl arsine oxide or aryl stibine oxide; and optionally, (b) contacting the oxide product of step (a) with a reducing agent to form the corresponding fluoropolyether-substituted aryl phosphine, aryl arsine, or aryl stibine. More specific embodiments are described hereinbelow.

DETAILED DESCRIPTION

Trademarks and trade names used herein are shown in upper case.

A common characteristic of fluoropolyethers is the presence of fluoroalkyl ether moieties. Perfluoropolyether is synonymous to perfluoropolyalkylether. Other synonymous terms frequently used include "PFPE", "PFPE oil", "PFPE fluid", and "PFPAE". Another useful fluorinated segment is a fluoroalkyl group.

The term "pnictogens" collectively indicates the elements in the Periodic Table of Elements belonging to Group V. Herein the term "pnictogens" is constrained to indicate the subset P, As, and Sb, and "triaryl pnictogens" collectively refers to triaryl phosphines, triaryl arsines and triaryl stibines. The triaryl pnictogens useful in the practice of the first step of the present invention are compounds described below.

The process of the present invention provides syntheses of mono-, di-, and tri-substituted fluoropolyether-substituted aryl and fluoroalkyl-substituted aryl phosphine, arsine, and stibine. For example, these compounds may have the structure of Formula 2:

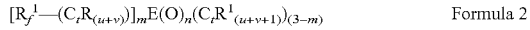

Formula 2 wherein
$R_f^1$ is a fluoropolyether or fluoroalkyl chain. Preferably, $R_f^1$ has a formula weight ranging from about 200 to about 15,000. Preferably, $R_f^1$ comprises repeat units. More preferably, $R_f^1$ is selected from the group consisting of:
(a) J-O—$(CF(CF_3)CF_2O)_c(CFXO)_dCFZ$-;
(b) $J^1$-O—$(CF_2CF_2O)_e(CF_2O)_fCFZ^1$-;
(c) $J^2$-O—$(CF(CF_3)CF_2O)_fCF(CF_3)CF_2$—;
(d) $J^3$-O—$(CQ_2\text{-}CF_2CF_2\text{—}O)_k$—$CQ_2\text{-}CF_2$—;
(e) $J^3$-O—$(CF(CF_3)CF_2O)_g(CF_2CF_2O)_h(CFXO)_i$—CFZ-;
(f) $J^4$-O—$(CF_2CF_2O)_rCF_2$—;
(g) $Q(C_pF_{2p})$—; and
(h) combinations of two or more thereof wherein J is a fluoroalkyl group selected from the group consisting of $CF_3$, $C_2F_5$, $C_3F_7$, $CF_2Cl$, $C_2F_4Cl$, $C_3F_6Cl$, and combinations of two or more thereof;

c and d are numbers such that the ratio of c:d ranges from about 0.01 to about 0.5;

X is F, $CF_3$, or combinations thereof;

Z is F, Cl or $CF_3$;

$J^1$ is a fluoroalkyl group selected from the group consisting of $CF_3$, $C_2F_5$, $C_3F_7$, $CF_2Cl$, $C_2F_4Cl$, and combinations of two or more thereof;

e and f are numbers such that the ratio of e:f ranges from about 0.3 to about 5;

$Z^1$ is F or Cl;

$J^2$ is $C_2F_5$, $C_3F_7$, or combinations thereof;

j is an average number such that the formula weight of $R_f$ ranges from about 400 to about 15,000;

$J^3$ is selected from the group consisting of $CF_3$, $C_2F_5$, $C_3F_7$, and combinations of two or more thereof;

k is an average number such that the formula weight of $R_f$ ranges from about 400 to about 15,000;

each Q is independently F, Cl, or H;

g, h and i are numbers such that (g+h) ranges from about 1 to about 50, the ratio of i:(g+h) ranges from about 0.1 to about 0.5;

$J^4$ is $CF_3$, $C_2F_5$, or combinations thereof;

r is an average number such that the formula weight of $R_f$ ranges from about 400 to about 15,000; and p is an integer from 4 to about 20 and $C_pF_{2p}$ is a linear divalent perfluoroalkyl radical;

each R and $R^1$ is independently H, a $C_1$-$C_{10}$ alkyl, a halogen, $OR^3$, OH, $SO_3M$, $NR^2_2$, $R^3OH$, $R^3SO_3M$, $R^3NR^2_2$, $R^3NO_2$, $R^3CN$, $C(O)OR^3$, $C(O)OM$, $C(O)R^3$, or $C(O)NR^2_2$, or combinations of two or more thereof;

wherein $R^2$ is independently H, $C_1$-$C_{10}$ alkyl, or combinations of two or more thereof;

$R^3$ is a $C_1$-$C_{10}$ alkyl; and

M is hydrogen or a metal, preferably not aluminum; more preferably, M is hydrogen or an alkali metal, still more preferably, M is hydrogen, sodium or potassium;

t is equal to (6+u);

u is any combination of 0, 2, 4, 6, 8, 10, 12, 14, 16;

v is independently either 2 or 4;

n is 0 or 1;

E is P, As, or Sb, preferably E is P; and m is greater than 0 to about 3.

The process of the present invention comprises a first step comprising contacting a fluoropolyether or fluoroalkyl primary bromide or iodide with a triaryl derivative of phosphorus (triaryl phosphine or triaryl phosphine oxide), arsenic (triaryl arsine or triaryl arsine oxide), or antimony (triaryl stibine or triaryl stibine oxide). Preferably a fluoropolyether or fluoroalkyl primary bromide or iodide is contacted with a triarylphosphine. Said contacting step is optionally performed in the presence of one or more of a radical initiator, a solvent, and a catalyst, to produce a corresponding fluoropolyether-substituted aryl or fluoroalkyl-substituted aryl phosphine oxide, fluoropolyether-substituted aryl or fluoroalkyl-substituted aryl arsine oxide, or fluoropolyether-substituted aryl or fluoroalkyl-substituted aryl stibine oxide. The process of the present invention, optionally, further comprises contacting the fluoropolyether- or fluoroalkyl-substituted aryl phosphine oxide, arsine oxide, or stibine oxide with a reducing agent to form a fluoropolyether- or fluoroalkyl-substituted aryl phosphine, arsine, or stibine.

In one particular embodiment, the pnictogen is phosphorous and a fluoropolyether or fluoroalkyl primary iodide is used and there is a ratio of the iodide to the triaryl phosphine of 3:1. In an alternative to this embodiment, there is a ratio of the iodide to the triaryl phosphine of 1:1. In either of these embodiments, the triaryl phosphine is preferably triphenylphosphine.

Fluoropolyether primary bromides or iodides useful in the first step of the present invention include, but are not limited to, those having the formulae of:

$F(C_3F_6O)_zCF(CF_3)CF_2Y;$

$F(C_3F_6O)_x(CF_2O)_wCF_2Y;$

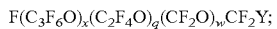

$F(C_3F_6O)_x(C_2F_4O)_q(CF_2O)_wCF_2Y;$

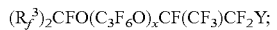

$(R_f^3)_2CFO(C_3F_6O)_xCF(CF_3)CF_2Y;$

$F(C_pF_{2p})Y;$ and combinations of two or more thereof;

wherein

Y is I or Br;

x is a number from 2 to about 100;

z is a number from about 3 to about 50, preferably from about 3 to about 25, more preferably from about 3 to about 10;

q is a number from 2 to about 50;

w is a number from 2 to about 50;

p is an integer from 4 to about 20 and $C_pF_{2p}$ is a linear divalent perfluoroalkyl radical;

each $R_f^3$ can be the same or different and is independently a monovalent $C_1$ to $C_{20}$ branched or linear fluoroalkane;

$C_3F_6O$ is linear or branched.

A preferred perfluoropolyether bromide or iodide has the formula $F(C_3F_6O)_zCF(CF_3)CF_2Y$ where Y and z are defined above.

Triaryl phosphines, triaryl arsines, and triaryl stibines useful in the first step of the present invention include, but are not limited to, compounds having the structure of Formula 3:

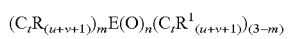

$(C_tR_{(u+v+1)})_mE(O)_n(C_tR^1_{(u+v+1)})_{(3-m)}$      Formula 3 wherein

E, R, $R^1$, t, u, v, m, and n are the same as defined for Formula 2, above. Preferably, E is P.

Preferred starting materials for the process of this invention are the triaryl phosphines, arsines and stibines; more preferred are triaryl phosphines, still more preferred is triphenyl phosphine or its oxide.

Suitable radical initiators for use in the first step include, but are not limited to, peroxides such as benzoyl peroxide and t-butyl peroxide. When used, a radical initiator is preferably added in two or more portions. The preferred initiator is benzoyl peroxide.

Suitable solvents include liquid aliphatic alcohols and carboxylic acids, preferably carboxylic acids, and more preferably, glacial acetic acid.

Suitable catalysts include any compound that promotes the formation of a fluoroalkyl or fluoropolyether free radical. Cupric acetate, ferric acetate, ferric chloride, or combinations of two or more thereof are examples of suitable catalysts. Cupric acetate is preferred. When used, the catalyst is typically present in an amount in the range of from about 0.0001 to about 5 weight %, based on the weight of the primary bromide or iodide compound.

The first step reaction is conducted at a temperature in the range of about 50° C. to about 210° C., preferably between about 70° to about 110° C. The reaction product is typically washed with a suitable organic solvent, for example, a 1:1 acetone:water mixture or glacial acetic acid, filtered, and stripped of volatile byproducts by distillation under reduced pressure to yield the fluoropolyether- or fluoroalkyl-substituted aryl phosphine oxide, aryl arsine oxide, or aryl stibine oxide.

The optional second step of the process of the present invention comprises contacting, in an inert solvent such as diethyl ether, the fluoropolyether- or fluoroalkyl-substituted aryl phosphine oxide, aryl arsine oxide or aryl stibine oxide with a reducing agent at a temperature from about 0° C. to about 12° C., preferably about 4° C. Lithium aluminum hydride, $LiAlH_4$ may be conveniently used. Optionally, prior to adding the reducing agent, the oxide may be contacted with an alkyl iodide such as methyl iodide, at ambient temperature, such as at about 25° C. This step may further comprise hydrolyzing the excess reducing agent, for example, $LiAlH_4$, with water or dilute hydrochloric acid, (for example, 2M HCl). This step may also further comprise washing the product with water and dilute HCl, and vacuum distilling the washed product. An inert fluorinated solvent is optionally used to aid transfer. Suitable inert fluorinated solvents are 1,1,2-trichlorotrifluoroethane or methyl perfluorobutyl ether (HFE-7100, available from 3M Corp., St. Paul, Minn.). This step may still further optionally comprise dissolving the distilled product in the same or a different inert fluorinated solvent, filtering, and redistilling under vacuum, to remove volatiles to yield the product.

While not wishing to be bound by theory, it is believed that the fluoropolyether- or fluoroalkyl-substitution occurs on the aryl substituent through a free radical mechanism similar to that described by Bravo et al. in *Journal of Organic Chemistry*, 62(21), 1997, pp. 7128-7136.

Compositions

The process of this invention provides some novel compositions of fluoropolyether- and fluoroalkyl-substituted pnictogen derivatives. More particularly, the compositions of this invention may have the structure Formula 2, as described hereinabove.

End Uses

The fluoropolyether-substituted aryl phosphines, aryl arsines, aryl stibines and corresponding oxides prepared according to the present invention are useful as additives to perfluoropolyether oils and greases for lubrication purposes under extreme temperature conditions, such as in military applications. In practice, a perfluoropolyether lubricant may comprise one or more of the fluoropolyether-substituted aryl phosphines, aryl arsines, aryl stibines and the oxides thereof prepared by processes of the present invention. The fluoropolyether-substituted aryl phosphines, aryl arsines, aryl stibines and the oxides are added to the perfluoropolyether lubricant in an amount of about 0.1 to about 5% by weight, based on the weight of the perfluoropolyether lubricant, and preferably from about 1 to about 2% by weight.

The fluoropolyether-substituted phosphines and fluoroalkyl-substituted phosphines prepared according to the present invention are useful as fluorous phase catalysts in hydroformylation reactions.

MATERIALS AND TEST METHODS

HFE-7100, methyl perfluorobutyl ether, is available from 3M Corp., St. Paul, Minn.

KRYTOX Iodide $[F(C_3F_6O)_zCF(CF_3)CF_2I$ where z has an average value of about 4-5] is produced by the methods described in U.S. Pat. No. 6,653,511, incorporated herein by reference.

Triaryl phosphines, stibines, and their derivatives are available from Sigma-Aldrich Chemical, Milwaukee, Wis.

CELITE 521 is a diatomaceous earth filter aid available from Sigma-Aldrich Chemical, Milwaukee, Wis.

Methods for testing the corrosion and oxidation inhibiting properties of the perfluoropolyether-substituted aryl phosphines, arsines and stibines prepared by the process of the present invention are as described in detail by Snyder et al. in U.S. Pat. Nos. 4,438,006 and 4,438,007, and by Christian et al. in U.S. Pat. Nos. 4,431,555, and 4,431,556. The test involves the immersion of steel, titanium, and other metals and alloys in formulations comprising 1% of the phosphine, arsine, or stibine, in a perfluorinated polyalkylether fluid. The metal samples are immersed in the formulations at temperatures of about 600° F. to about 650° F. (316-343° C.) as air is bubbled through the formulation to create an oxidizing environment. For the examples tested hereinbelow (Comparative Example and Example 3), the metal samples are immersed in 1% formulations of the Comparative Example or Example 3 in a perfluoropolyether oil. The tests are performed at 300° C. (572° F.), 315° C. (599° F.), and 330° C. (626° F.). The change in the metal sample weight per unit surface fluoropolyether-substituted aryl phosphines effectively eliminates significant corrosion of the metal with degradation of the lubricant observed in the absence of the additive.

The perfluoroalkylether-substituted aryl phosphine, $[F(C_3F_6)OCF(CF_3)CF_2OCF(CF_3)CF_2—C_6H_4]_3P$, prepared according to the synthetic procedure described in U.S. Pat. No. 4,454,349, Example 1, is used as the Comparative Example.

EXAMPLES

Example 1

Preparation of $[F(CF(CF_3)CF_2O)_zCF(CF_3)CF_2—C_6H_4]_3P=O$

A flask is charged with $F(CF(CF_3)CF_2O)_zCF(CF_3)CF_2I$ (200 g, 0.16 mol, $z_{avg}$=4.3), glacial acetic acid (200 mL), copper(II) acetate (0.60 g, 0.0032 mol), and triphenylphosphine (14.4 g, 0.0552 mol). The reaction mass is stirred and heated to 70° C., then benzoyl peroxide (38 g) is added, and the temperature raised to 90° C. Two more additions of benzoyl peroxide (each 38 g) are made in 40-minute intervals, for a total of 114 g. When GC/MS analysis indicates all the iodide is reacted, the crude product is then washed three times with 200 mL of 1:1 water:acetone solution and purified by oil pump vacuum (1 mmHg, 130 Pa) distillation at 120° C. The sample is then filtered through a Büchner funnel with a 0.25 inch (6.4 mm) layer of CELITE 521 (see MATERIALS) on a WHATMAN #1 filter paper, yielding 138 g (71% yield). Further purification by distillation at 220° C. using a molecular drag pump (0.1 mmHg, 13 Pa) on 88 g of the sample to eliminate byproducts yields purified $[F(CF(CF_3)CF_2O)_zCF(CF_3)CF_2—C_6H_4]_3P=O$, as evidenced by $^1H$, $^{19}F$, and $^{31}P$ NMR, and semi-quantitative X-Ray Fluorescence (XRF) (P=0.750±0.038%) (44 g, 35.5%).

Example 2

Preparation of $[F(CF(CF_3)CF_2O)_zCF(CF_3)CF_2—C_6H_4]_3P=O$

A flask is charged with $F(CF(CF_3)CF_2O)_zCF(CF_3)CF_2I$ (50 g, 0.042 mol, $z_{avg}$=4.3) and triphenylphosphine (3.91 g, 0.015 mol). The reaction mass is stirred and heated to 210° C. for 24 hours. The reaction is complete when GC/MS analysis indicates all the iodide is reacted. The desired product, $[F(CF(CF_3)CF_2O)_zCF(CF_3)CF_2—C_6H_4]_3P=O$, is obtained, as evidenced by $^1H$, $^{19}F$, and $^{31}P$ NMR.

Example 3

Reduction of [F(CF(CF$_3$)CF$_2$O)$_z$CF(CF$_3$)CF$_2$—C$_6$H$_4$]$_3$P=O

To [F(CF(CF$_3$)CF$_2$O)$_z$CF(CF$_3$)CF$_2$—C$_6$H$_4$]$_3$P=O (492.75 g, 0.134 mol, $z_{avg}$=4.8 prepared as in Example 1) is added anhydrous diethyl ether (500 mL) at room temperature with stirring. Methyl iodide (9.16 mL, 0.147 mol) is then added and the mixture stirred for 3 hours. The reaction vessel is then cooled to 4° C. using an ice water bath, and a 1M LiAlH$_4$ solution in diethyl ether (335 mL, 0.335 mol) is slowly added using an addition funnel. After stirring for 4 hours at 4° C., the excess LiAlH$_4$ is hydrolyzed using 500 mL of water. The aqueous layer is drawn off, and the mixture is then subsequently washed with 500 mL 2M HCl twice. HFE-7100 (20 mL) is then added to aid transfer to a distilling flask. The product is distilled at 120° C. with oil pump vacuum (1 mmHg, 0.13 kPa.), yielding [F(CF(CF$_3$)CF$_2$O)$_n$CF(CF$_3$)CF$_2$—C$_6$H$_4$]$_3$P, as evidenced by $^1$H, $^{19}$F, and $^{31}$P NMR, and semi-quantitative XRF (P=0.983±0.049%) (482.97 g, 98.0%).

Example 4

Preparation of [F(CF(CF$_3$)CF$_2$O)$_z$CF(CF$_3$)CF$_2$—C$_6$H$_4$][C$_6$H$_5$]$_2$P=O A flask is charged with F(CF(CF$_3$)CF$_2$O)$_z$CF(CF$_3$)CF$_2$I (50 g, 43 mmol, $z_{avg}$=5.43), glacial acetic acid (500 mL), and triphenylphosphine (67.77 g, 280 mmol). The reaction mass is stirred and heated to 70° C., then benzoyl peroxide (10 g) is added, and the temperature raised to 90° C. Five more additions of benzoyl peroxide (each 10 g) are made in 1.5-hour intervals, for a total of 60 g. When GC/MS analysis indicates all the iodide was reacted, the crude product is then washed three times with 200 mL of 1:1 water:acetone solution and purified by oil pump vacuum (1 mmHg, 130 Pa) distillation at 120° C. The sample is then filtered through a CELITE 521 bed as in Example 1. Further purification by distillation at 220° C. using a molecular drag pump (0.1 mmHg, 13 Pa) eliminates poly-HFPO byproducts, yielding purified

[F(CF(CF$_3$)CF$_2$O)$_z$CF(CF$_3$)CF$_2$—C$_6$H$_4$][C$_6$H$_5$]$_2$P=O, as evidenced by $^1$H, $^{19}$F, and $^{31}$P NMR and semi-quantitative XRF (P=2.67±0.08%) (19.55 g, 30.5%).

Example 5

Reduction of [F(CF(CF$_3$)CF$_2$O)$_z$CF(CF$_3$)CF$_2$—C$_6$H$_4$][C$_6$H$_5$]$_2$P=O To [F(CF(CF$_3$)CF$_2$O)$_z$CF(CF$_3$)CF$_2$—C$_6$H$_4$][C$_6$H$_5$]$_2$P=O (10.7 g, 7.2 mmol, $z_{avg}$=5.29 prepared as in Example 4) is added anhydrous diethyl ether (12 mL) at room temperature with stirring. Methyl iodide (0.577 mL, 9.4 mmol) is then added and the mixture stirred for 2 hours. The reaction vessel is then cooled to 4° C. using an ice water bath, and a 1M LiAlH$_4$ solution in diethyl ether (21.5 mL, 21.5 mmol) is slowly added using an addition funnel. After stirring for 4 hours at 4° C., the excess LiAlH$_4$ is hydrolyzed using 40 mL of water. The aqueous layer is drawn off, and the mixture is then subsequently washed with 40 mL water, then twice with 40-mL portions of 5% HCl. HFE-7100 (20 mL) is then added to aid transfer to a distilling flask. The crude product is distilled at 100° C. with oil pump vacuum (1 mmHg, 130 Pa). The product is then re-dissolved in HFE-7100 (20 mL) and filtered in a Büchner funnel through WHATMAN #1 filter paper to eliminate solid impurities. The product is re-distilled at 115° C. with oil pump vacuum (1 mmHg, 130 Pa) for 2 h, yielding [F(CF(CF$_3$)CF$_2$O)$_z$CF(CF$_3$)CF$_2$—C$_6$H$_4$][C$_6$H$_5$]$_2$P=O, as evidenced by $^1$H, $^{19}$F, and $^{31}$P NMR, and semi-quantitative XRF (P=3.50±0.09%) (7.44 g, 69.5%).

Example 6

Preparation of [F(CF(CF$_3$)CF$_2$O)$_z$CF(CF$_3$)CF$_2$—C$_6$H$_4$]$_3$Sb=O

A flask is charged with F(CF(CF$_3$)CF$_2$O)$_z$CF(CF$_3$)CF$_2$I (50 g, 42 mmol, $z_{avg}$=4.27), glacial acetic acid (50 mL), Copper(II) acetate (0.15 g, 0.8 mmol), and triphenylantimony (4.77 g, 13.5 mmol). The reaction mass is stirred and heated to 70° C., then benzoyl peroxide (5 g) is added, and the temperature raised to 90° C. Five more additions of benzoyl peroxide (each 5 g) are made in 1.5-hour intervals, for a total of 30 g. When GC/MS analysis indicates all the iodide is reacted, the crude product is then washed three times with 100 mL of 1:1 water:acetone solution and purified by oil pump vacuum (1 mmHg, 130 Pa) distillation at 120° C. The sample is then filtered through a Büchner funnel with a 0.25 inch (6.4 mm) layer of CELITE 521 (see MATERIALS) on a WHATMAN #1 filter paper, yielding 29.1 g (64.5%). Further purification by distillation at 220° C. using a molecular drag pump (0.1 mmHg, 13 Pa) eliminates poly-HFPO byproducts, yielding purified [F(CF(CF$_3$)CF$_2$O)$_z$CF(CF$_3$)CF$_2$—C$_6$H$_4$]$_3$Sb=O, as evidenced by $^1$H, $^{19}$F, and $^{31}$P NMR, and semi-quantitative XRF (Sb=3.02±0.20%) (13.52 g, 29.9%).

Example 7

Reduction of [F(CF(CF$_3$)CF$_2$O)$_z$CF(CF$_3$)CF$_2$—C$_6$H$_4$]$_3$Sb=O

To [F(CF(CF$_3$)CF$_2$O)$_z$CF(CF$_3$)CF$_2$—C$_6$H$_4$]$_3$Sb=O (5.0 g, 7.2 mmol, $z_{avg}$=5.29 prepared as in Example 6) is added anhydrous diethyl ether (5 mL) at room temperature with stirring. Methyl iodide (0.10 mL, 1.63 mmol) is then added and the mixture stirred for 3 hours. The reaction vessel is then cooled to 4° C. using an ice water bath, and a 1M LiAlH$_4$ solution in diethyl ether (3.4 mL, 3.4 mmol) is slowly added using an addition funnel. After stirring for 4 hours at 4° C., the excess LiAlH$_4$ is hydrolyzed using 20 mL of water. The aqueous layer is drawn off, and the mixture is then subsequently washed twice with 50 mL of 5% HCl. HFE-7100 (10 mL) is then added to aid transfer to a distilling flask. The product is distilled at 115° C. with oil pump vacuum (1 mmHg, 0.13 kPa), yielding [F(CF(CF$_3$)CF$_2$O)$_z$CF(CF$_3$)CF$_2$—C$_6$H$_4$]$_3$Sb, as evidenced by $^1$H and $^{19}$F NMR, and semi-quantitative XRF (Sb=1.07±0.08%) (3.67 g, 73.4%).

Example 8

Preparation of [F(CF(CF$_3$)CF$_2$O)$_z$CF(CF$_3$)CF$_2$—C$_6$H$_3$(ortho-CH$_3$)]$_3$P=O A flask is charged with F(CF(CF$_3$)CF$_2$O)$_z$CF(CF$_3$)CF$_2$I (50 g, 42 mmol, $z_{avg}$=4.3), glacial acetic acid (50 mL), copper (II) acetate (0.15 g, 0.8 mmol), and tri-ortho-tolylphosphine (4.10 g, 13.5 mmol). The reaction mass is stirred and heated to 70° C., then benzoyl peroxide (5 g) is added, and the temperature raised to 90° C. Two more additions of benzoyl peroxide (each 5 g) are made in 1.5-hour intervals, for a total of 15 g. When GC/MS analysis indicates all the iodide is reacted, the crude product is then washed three times with 100 mL of 1:1 water:acetone solution and purified by oil pump vacuum distillation (1 mmHg, 130 Pa) at 120° C. The sample is then filtered through a Büchner funnel with a 0.25 inch (6.4 mm) layer of CELITE 521 (see MATERIALS) on a WHATMAN #1 filter paper, yielding 19.18 g (43.1%). Further purification by distillation at 220° C. using a molecular drag pump (0.1 mmHg, 130 Pa) eliminates poly-HFPO byproducts, yielding purified $[F(CF(CF_3)CF_2O)_zCF(CF_3)CF_2C_6H_3(\text{ortho-}CH_3)]_3P{=}O$, as evidenced by $^1H$, $^{19}F$, and $^{31}P$ NMR, and semi-quantitative XRF (P=1.37±0.06%) (9.75 g, 21.9%).

Example 9

Preparation of $[F(CF(CF_3)CF_2O)_zCF(CF_3)CF_2{-}C_6H_3(\text{ortho-}CH_3)][F(CF(CF_3)CF_2O)_zCF(CF_3)CF_2{-}C_6H_4]_2P{=}O$ A flask is charged with $F(CF(CF_3)CF_2O)_zCF(CF_3)CF_2I$ (50 g, 42 mmol, $z_{avg}$=4.27), glacial acetic acid (50 mL), and diphenyl(ortho-tolyl)phosphine (3.87 g, 14 mmol). The reaction mass was stirred and heated to 70° C., then benzoyl peroxide (5 g) was added, and the temperature was raised to 90° C. Two more additions of benzoyl peroxide (each 5 g) were made in 1.5-hour intervals, for a total of 15 g. When GC/MS analysis indicated all the iodide was reacted, the crude product was then washed twice with 40 mL of glacial acetic acid. The glacial acetic acid washes were then extracted with 30 mL HFE-7100, the extracts added to the product layer, and purified by oil pump vacuum (1 mmHg, 0.13 kPa) distillation at 120° C. Further purification by distillation at 220° C. using a molecular drag pump (0.1 mmHg, 0.013 kPa) was effected to eliminate poly-HFPO byproducts, yielding purified $[F(CF(CF_3)CF_2O)_zCF(CF_3)CF_2{-}C_6H_3(\text{ortho-}CH_3)][F(CF(CF_3)CF_2O)_zCF(CF_3)CF_2{-}C_6H_4]_2P{=}O$, as evidenced by $^1H$, $^{19}F$, and $^{31}P$ NMR, and semi-quantitative XRF (P=1.36±0.06%) (21.02 g, 42.0%).

TEST RESULTS

The test results below show both Comparative Example 1 (Comp. Ex.) and the product of the new process (Example 3) to be equivalent. In the Table, % Viscosity Change, Acid Number Change, Fluid Loss and Metal Weight Change are given as average values over a number of trials.

TABLE

| Product Tested (a) | Test Temp. °C. | % Viscosity Change @ 40° C. | Acid Number mg KOH/g metal Wt Change | Fluid Loss % Wt Loss | Metal Weight Change (mg/cm$^2$) 4140 Steel |
|---|---|---|---|---|---|
| Comp. Ex. in DEMNUM S-65 (b) | 300 | 0.45 | 0.00 | 0.00 | 0.10 |
| Example 3 in DEMNUM S-65 (b) | 300 | 1.35 | 0.00 | 0.00 | 0.06 |
| Comp. Ex. in DEMNUM S-65 (b) | 315 | 0.55 | 0.00 | 0.00 | 0.43 |
| Example 3 in DEMNUM S-65 (b) | 315 | 1.70 | 0.00 | 0.52 | 0.08 |
| Comp. Ex. in KRYTOX 143AC (c) | 315 | 5.65 | Not Determined | 0.00 | −0.02 |
| Example 3 in KRYTOX 143AC (c) | 315 | 10.23 | 0.00 | 1.46 | 0.06 |
| Comp. Ex. in KRYTOX 143AC (c) | 330 | 3.69 | 0.00 | 0.79 | 1.95 |
| Comp. Ex. in KRYTOX 143AC (c) | 330 | 3.88 | 0.00 | 0.69 | 1.00 |
| Comp. Ex. in KRYTOX 143AC (c) | 330 | 5.20 | Not Determined | 0.00 | −1.56 |
| Example 3 in KRYTOX 143AC (c) | 330 | 10.53 | 0.00 | 0.93 | 0.96 |

| Product Tested (a) | Metal Weight Change (mg/cm$^2$) | | | | Fluid Appearance |
|---|---|---|---|---|---|
| | 52100 Bearing Steel | 410 Stainless Steel | M50 Tool Steel | 440C Stainless Steel | |
| Comp. Ex. in DEMNUM S-65 (b) | 0.10 | 0.02 | 0.26 | 0.00 | Not Determined |
| Example 3 in DEMNUM S-65 (b) | 0.04 | 0.02 | 0.05 | 0.01 | No Change |
| Comp. Ex. in DEMNUM S-65 (b) | 0.46 | 0.10 | 0.91 | 0.91 | Not Determined |
| Example 3 in DEMNUM S-65 (b) | 0.09 | 0.02 | 0.12 | 0.04 | No Change |
| Comp. Ex. in KRYTOX 143AC (c) | 0.07 | 0.05 | 0.05 | 0.05 | No Change |
| Example 3 in KRYTOX 143AC (c) | 0.05 | 0.01 | 0.13 | 0.03 | No Change |
| Comp. Ex. in KRYTOX 143AC (c) | 0.07 | 0.05 | 0.01 | 0.01 | Hazy with metal particles |
| Comp. Ex. in KRYTOX 143AC (c) | 0.06 | 0.00 | 0.11 | 0.09 | No Change |

TABLE-continued

| | | | | | |
|---|---|---|---|---|---|
| Comp. Ex. in KRYTOX 143AC (c) | 0.04 | −0.07 | −1.93 | −0.36 | No Change |
| Example 3 in KRYTOX 143AC (c) | 0.32 | 0.03 | 0.53 | 0.07 | No Change |

(a) Each Product Tested was a formulation containing 1% of the product from either the Comparative Example or Example 3 in the specified perfluoropolyether oil.
(b) DEMNUM S-65 is a perfluoropolyether oil available from Daikin Industries, Osaka, Japan.
(c) KRYTOX 143AC is a perfluoropolyether oil available from E. I. du Pont de Nemours and Company, Wilmington, DE.

What is claimed is:

1. A process to prepare a fluoropolyether- or fluoroalkyl-substituted aryl stibine comprising contacting a compound selected from the group consisting of fluoropolyether primary bromide, fluoropolyether primary iodide, fluoroalkyl primary bromide and fluoroalkyl primary iodide, with a triaryl stibine or triaryl stibine oxide to produce the corresponding mono-substituted, di-substituted, tri-substituted, or a combination of two or more thereof, fluoropolyether- or fluoroalkyl-substituted aryl stibine oxide, wherein the process is performed in the presence of one or more of a radical initiator, a solvent and a catalyst.

2. The process of claim 1 further comprising contacting the oxide product with a reducing agent to form the corresponding fluoropolyether- or fluoroalkyl-substituted aryl stibine.

3. The process of claim 1 wherein the triaryl stibine is triphenylstibine.

4. The process of claim 1 performed in the presence of a radical initiator and further wherein the radical initiator is a peroxide.

5. The process of claim 4 wherein the radical initiator is benzoyl peroxide or t-butyl peroxide.

6. The process of claim 1 performed in the presence of a solvent and further wherein the solvent is a liquid aliphatic alcohol or a carboxylic acid.

7. The process of claim 6 wherein the solvent is glacial acetic acid.

8. The process of claim 1 performed at a temperature of about 50° C. to about 210° C.

9. The process of claim 8 is performed at a temperature of about 70° C. to about 110° C.

10. The process of claim 2 wherein the reducing agent is lithium aluminum hydride.

11. The process of claim 10 wherein the reducing step is performed at a temperature from about 0° C. to about 12° C.

12. The process of claim 11 wherein the reducing step is performed at a temperature of about 4° C.

13. The process of claim 2 wherein, prior to the reducing step, the oxide is contacted with an alkyl iodide.

14. The process of claim 13 wherein the alkyl iodide is methyl iodide.

15. The process of claim 1 wherein a fluoropolyether primary iodide or fluoroalkyl primary iodide is contacted with a triaryl stibine or triaryl stibine oxide.

16. The process of claim 15 wherein the iodide has the formula $F(C_3F_6O)_zCF(CF_3)CF_2Y$ wherein Y is I and z is 3 to 50.

17. The process of claim 15 wherein the iodide has the formula $F(C_pF_{2p})Y$ wherein Y is I and p is from 4 to about 20.

18. The process of claim 16 or 17 wherein the iodide is contacted with a triaryl stibine.

19. The process of claim 18 wherein the triaryl stibine is triphenyl stibine.

20. The process of claim 19 wherein the ratio of the iodide to the stibine is 3:1.

21. The process of claim 19 wherein the ratio of the iodide to the stibine is 1:1.

* * * * *